United States Patent [19]
Hagiwara

[11] Patent Number: 5,116,308
[45] Date of Patent: May 26, 1992

[54] APPARATUS FOR PROCESSING FLUID AND METHOD OF DRIVING THE SAME

[75] Inventor: Kazuhiko Hagiwara, Fuji, Japan

[73] Assignee: Terumo Kabushiki Kaisha, Tokyo, Japan

[21] Appl. No.: 463,271

[22] Filed: Jan. 10, 1990

[30] Foreign Application Priority Data

Jan. 13, 1989 [JP] Japan .................................. 1-7068
Apr. 13, 1989 [JP] Japan .................................. 1-93558

[51] Int. Cl.⁵ ............................................. A61M 1/00
[52] U.S. Cl. ........................................ 604/4; 604/5; 422/46
[58] Field of Search ................................ 422/46-48; 604/4-6; 128/DIG. 3

[56] References Cited

U.S. PATENT DOCUMENTS

| | | |
|---|---|---|
| 3,898,045 | 8/1975 | Bowley ................ 128/DIG. 3 X |
| 4,451,562 | 5/1984 | Elgas et al. ............. 422/46 X |
| 4,469,659 | 9/1984 | Carson et al. .............. 422/46 |
| 4,490,331 | 12/1984 | Steg, Jr. .................. 422/46 |
| 4,564,359 | 1/1986 | Ruhland . | |
| 4,573,992 | 3/1986 | Marx . | |
| 4,642,088 | 4/1987 | Gunter . | |
| 4,808,378 | 2/1989 | Nakanishi et al. ........... 422/48 |
| 4,874,581 | 10/1989 | Sutherland et al. .......... 422/46 |
| 4,971,836 | 11/1990 | Fukasawa et al. ....... 128/DIG. 3 X |
| 4,975,247 | 12/1990 | Bodolato et al. ............. 422/48 |

FOREIGN PATENT DOCUMENTS

| | | |
|---|---|---|
| 0094682 | 11/1983 | Fed. Rep. of Germany . |
| 0116352 | 8/1984 | Fed. Rep. of Germany . |
| 233943A5 | 3/1986 | Fed. Rep. of Germany . |
| 63-177863 | 7/1988 | Japan . |

Primary Examiner—Robert A. Hafer
Assistant Examiner—Kerry Owens
Attorney, Agent, or Firm—Frishauf, Holtz, Goodman & Woodward

[57] ABSTRACT

Fluid in- and out-flow spaces are provided for fluid inlet and outlet of a fluid processor accommodated in housing. Further, pair wall means defining the fluid in- and out-flow spaces, a flexible member provided for deformation on at least one of the wall means, an operation chamber provided in correspondence to the flexible member, fluid pressure supply means for fluid pressure for reciprocating the flexible member and port on-off means for reverse flow prevention to direct flow of fluid from the fluid in-flow space to the fluid out-flow space are provided. Reciprocal operation of the flexible member generates fluid pressure variation in the fluid in- and out-flow spaces, thus causing flow of said fluid processor.

26 Claims, 15 Drawing Sheets

APPARATUS FOR PROCESSING FLUID AND METHOD OF DRIVING THE SAME

BACKGROUND OF THE INVENTION

This invention relates to an apparatus for processing fluid such as oxygenator and dialyser and, more particularly, to an apparatus for processing fluid for pumping fluid through a fluid processor and a method of driving the same apparatus.

In a prior art apparatus for processing fluid, for example a hollow fiber type oxygenator used for effecting gas exchange between carbon dioxide in blood and oxygen, uses a roller pump as blood circulation pump. This pump is provided separately from the oxygenator body.

With the prior art hollow fiber type oxygenator, however, it is necessary in use to connect the oxygenator body and roller pump to each other with tubing or tubes to assemble a system. The assembling is very time-consuming and cumbersome. In addition, an increased area of the system is necessary for setting the system. Further, when the roller pump is used, cracking is liable to be generated in tubes due to squeezing of tubes for long time, thus giving rise to such problems as leakage and contamination of blood. Further, blood is liable to be stagnated in blood in- or out-flow space. Particularly, in extracorporeal circulation without use of any agglomeration-resistant agant, thrombus is generated due to such blood stagnation, leading to hazardous clogging of the hollow fibers of the oxygenator.

Further, in ECMO (extracorporeal membrane oxygenation), which mostly uses V-A and V-V bypasses, with the use of the roller pump a vein reserver or a negative pressure absorption chamber is provided to buffer excessive suction due to forced blood removal by the roller pump and then prevent sticking of cateter for blood removal to the vein wall. Such vein reserver or negative pressure absorption chamber, however, can not be provided in the case of extracorporeal circulation without use of any agglomeration-resistant agent because of possible generation of thrombus due to stagnation of blood in the circuit.

SUMMARY OF THE INVENTION

The present invention has been intended in the light of the above, and its object is to provide an apparatus for processing fluid, which permits reduction of area necessary for installing system, permits ready assembling of the system and can prevent generation of stagnation of fluid to prevent various adverse effects due to such stagnation.

To attain the above object of the invention, there is provided an apparatus for processing fluid, which comprises a housing, a fluid processor accommodated in the housing and having a fluid in-flow port and a fluid out-flow port, fluid in- and out-flow spaces respectively provided for the respective fluid in- and out-flow ports and having respective fluid ports, pair wall means defining the respective fluid in- and out-flow spaces, and flexible member provided for deformation or transformation on at least one of the wall means and capable of being reciprocally deformed to cause fluid pressure variations, an operation chamber provided in correspondence to the flexible member, fluid pressure supply means for supplying fluid pressure to the operation chamber for causing reciprocal operation of the flexible member, and pair port on-off means for reverse flow prevention, for communicating and blocking the fluid ports and directing the flow of fluid from the fluid in-flow space to the fluid out-flow space.

In the above apparatus, the fluid processor is provided with a hollow fiber bundle.

According to the invention, the port on-off means may have a check valve.

With the apparatus for processing fluid having the above construction according to the invention, when fluid pressure is supplied into the operation chamber by the fluid pressure supply means, the flexible member is reciprocated to cause pressure variations of fluid in the fluid of in-flow space and/or out-flow space. Thus, with the pressure variations and function of the port onoff means fluid introduced through the fluid port is caused to flow through the fluid in-flow port and fluid processor and thence through the fluid out-flow port and fluid port. More specifically, fluid passes through the fluid in-flow space side fluid port and fluid processor to flow smoothly to the fluid outflow space side fluid port, thus eliminating stagnation in the fluid in-and out-flow spaces.

Where the apparatus in used as oxygenator, milder blood removal can be obtained by controlling the pressure in the operation chamber. Thus, there is no necessity of providing either vein reserver or negative pressure prevention chamber in the extracorporeal circuit. Thus, it is possible to further reduce stagnant zone in the entire extracorporeal circuit.

Further, by arranging such that blood flows downwardly through the oxygenator, with flexible member provided in the blood in-flow space to cause blood to be introduced into the in-flow space with its head, blood flows such that it is forces out at all time. Therefore, there is no possibility of generation of negative pressure in blood in the apparatus.

According to the invention, there is also provided an apparatus for processing fluid, in which the port on-off means includes first on-off means for communicating and blocking the fluid in-flow space port and second on-off means for communicating and blocking the fluid out-flow space fluid port, and the fluid pressure supply means includes a first pressure source for providing a positive fluid pressure to the operation chamber, a second pressure source for providing a negative or atmospheric fluid pressure to the operation chamber, a first pressure supply flow path for communicating the first pressure source and the operation chamber with each other, a second pressure supply flow path for communicating the second pressure source and the operation chamber with each other, and switching means for switching the first and second pressure supply flow paths for communication and blocking.

With this apparatus for processing fluid, fluid flows more smoothly from the fluid in-flow space fluid port to the fluid out-flow space fluid port, and it is possible to effectively prevent stagnation of fluid in the fluid in- and out-flow spaces.

According to the invention, there is further provided an apparatus, which further comprises control means for driving the port on-off means and fluid pressure supply means by sequentially and repeatedly executing a first step of rendering the first on-off means to be in a closed state, a second step executed subsequent to the first step to render the second on-off means to be in an open state and switch the fluid in-flow space side switching means to the first pressure supply flow path, a third step of rendering the second on-off means to be in a closed state, a fourth step executed subsequent to the third step to render the first on-off means to be in an open state, and a fifth step executed subsequent to the third and fourth steps to switch the switching means to the second pressure supply flow path.

According to the invention, there is further provided an apparatus for processing fluid, in which the control means drives the port on-off means and fluid pressure supply means further performs other steps of blocking both the flow paths with the switching means after the second step and before the third step and also after the fifth step and before the first step.

According to the invention, there is further provided an apparatus for processing fluid, in which the switching means includes first switching means on the side of the fluid in-flow space and second switching means on the side of the fluid out-flow space, and which further comprises control means for driving the port on-off means and fluid pressure supply means being driven by sequentially and repeatedly executing a first step of rendering the first on-off means to be in a closed state, a second step of switching the second switching means to the second pressure supply flow path and switching the first switching means to the first pressure supply flow path, a third step of rendering the second on-off means to be in an open state and switching the second switching means to the first pressure supply flow path, a fourth step of rendering the second on-off means to be in a closed state, a fifth step of rendering the first on-off means to be in an open state, and a sixth step of switching the first switching means to the second pressure supply flow path.

According to the invention, there is further provided an apparatus for processing fluid, in which the control means drives the port on-off means and fluid pressure supply means by further executing a step of blocking both the flow paths with the first switching means and a step of blocking both the flow paths with the second switching means after the second step and before the third step, a step of blocking both the flow paths with the second switching means after the third step and before the fourth step and a step of blocking both the flow paths after the sixth step and before the first step.

According to the invention, there is further provided an apparatus for processing fluid, in which the switching means includes first switching means on the side of the fluid in-flow space and second switching means on the side of the fluid out-flow space, and which further comprises control means for controlling the port on-off means and fluid pressure supply flow means by sequentially and repeatedly executing a first step of rendering the first on-off means to be in a closed state, a second step of rendering the second on-off means to be in an open state, switching the first switching means to the first pressure supply flow path and switching the second switching means to the first pressure supply flow path, a third step of rendering the second on-off means to be in a closed state, a fourth step of rendering the first on-off means to be in an open state, a fifth step of switching the first switching means to the second pressure supply flow path, and a sixth step of switching the second switching means to the second pressure supply flow path.

According to the invention, there is further provided an apparatus for processing fluid, in which the control means drives the port on-off means and fluid pressure supply flow path by further executing a step of blocking both the flow paths with the first switching means and a step of blocking both the flow paths with the second switching means after the second step and before the third step and a step of blocking both the flow paths with the first switching means and a step of blocking both the flow paths with the second switching means after the sixth step and before the first step.

According to the invention, there is further provided an apparatus for processing fluid, which comprises a housing, a fluid processor accommodated in the housing and having a fluid in-flow port and a fluid out-flow port, fluid in- and out-flow spaces provided for the respective fluid in- and out-flow ports and having respective fluid ports, pair wall means defining the respective fluid in- and out-flow spaces, a flexible member provided for deformation or transformation on the wall means defining the fluid in-flow space and capable of being reciprocally operated to generate pressure variations in fluid, an operation chamber provided in correspondence to the flexible member, fluid pressure supply flow means for providing a fluid pressure to the operation chamber for causing reciprocal operation of the flexible member, port on-off means for communicating and blocking the respective fluid ports and directing flow of fluid from the fluid in-flow space to the fluid out-flow space, the port on-off means including first on-off means for communicating and blocking the fluid inflow space fluid port and a second on-off means for communicating and blocking the fluid out-flow space fluid port, the fluid pressure supply means including a first pressure source for providing a fluid positive pressure to the operation chamber, a second pressure source for providing a negative or atmospheric fluid pressure to the operation chamber, a first pressure supply flow path for communicating the first pressure source and the operation chamber with each other, a second pressure supply flow path for communicating the second pressure source and the operation chamber with each other, first communicating/blocking means for communicating and blocking the first pressure supply flow path and second communicating/blocking means for communicating and blocking the second pressure supply flow path, the apparatus further comprising control means for driving the port on-off means and the fluid pressure supply means by sequentially and repeatedly executing a first step of rendering the first on-off means to be in a closed state, a second step of blocking the second communicating/blocking means after the first step, a third step of rendering the second on-off means to be in an open state after the second step, a fourth step of communicating the first communicating/blocking means after the third step, a fifth step for substantially simultaneously rendering the second on-off means to be in a closed state, blocking the first communicating/blocking means and communicating the second communicating/blocking means after the fourth step and a sixth step of rendering the first on-off means to be in an open state after the fifth step.

Further, according to the invention there is provided a method of driving an apparatus for processing fluid passed through the fluid processor, comprising a first step of rendering the first on-off means to be in a closed state, a second step of rendering the second on-off means to be in an open state and switching the fluid in-flow space side switching means to the first pressure supply flow path after the first step, a third step of rendering the second on-off means to be in a closed state, a fourth step of rendering the first on-off means to be in an open state after the third step and a fifth step for switching the switching means to the second pressure supply flow path after the third and fourth steps, these steps being executed sequentially and repeatedly.

According to the invention, there is further provided a method of driving an apparatus for processing fluid, which further comprises the steps of blocking both the flow paths with the switching means after the second step and before the third step and also after the fifth step and before the first step.

In this method of driving, by switching the switching means to the first pressure supply flow path positive pressure is produced in the operation chamber, and thus the flexible member is pushed. Conversely, by switching the switching means to the second pressure to the second pressure supply flow path, negative/atmospheric pressure is produced in the operation chamber, and thus the flexible member is pulled. Thus, with the first step of rendering the in-flow side first on-off means to be in a closed state and the second step of out-flow side second on-off means to be in an open state and switching the in-flow side switching means to the first pressure supply flow path after the first step, fluid in the fluid in-flow space is forced through the fluid processor into the fluid out-flow space to be led out through the fluid port, and with the third step of rendering the second on-off means to be in a closed state, fourth step of rendering the first on-off means to be in an open state after the third step and fifth step of switching the switching means to the second pressure supply flow path after the fourth step fluid is introduced into the fluid in-flow space through the fluid port.

According to the invention, there is further provided a method of driving an apparatus for processing fluid passed through the processor, in which the switching means includes first switching means on the fluid in-flow space side and second switching means on the fluid out-flow space side, and which comprises a first step of rendering the first on-off means to be in a closed state, a second step of switching the second switching means to the second pressure supply flow path and switching the first switching means to the first pressure supply flow path, a third step of rendering the second on-off means to be in an open state and switching the second switching means to the first pressure supply flow path, a fourth step of rendering the second on-off means to be in a closed state, a fifth step of rendering the first on-off means to be in an open state and a sixth step of switching the first switching means to the second pressure supply flow path, these steps being executed sequentially and repeatedly.

According to the invention, there is further provided a method of driving an apparatus for processing fluid, which further comprises a step of blocking both the flow paths with the first switching means and a step of blocking both the flow paths with the second switching means after the second step and before the third step, a step of blocking both the flow paths with the second switching means after the third step and before the fourth step and a step of blocking both the flow paths with the first switching means after the sixth step and before the first step.

In this method, with the first step of rendering the first on-off means to be in a closed state and second step of switching the second switching means to the second pressure supply flow path and switching the first switching means to the first pressure supply flow path fluid in the fluid in-flow space is forced through the fluid processor into the fluid out-flow space, with the third step of switching the second on-off means to be in an open state and switching the second switching means to the first pressure supply flow path fluid in the fluid out-flow space is led out through the blood port, and with the fourth step of rendering the second on-off means to be in a closed state, fifth step of rendering the first on-off means to be in an open state and sixth step of switching the first switching means to the second pressure supply flow path fluid is introduced into the fluid in-flow space through the fluid port.

According to the invention, there is further provided a method of driving an apparatus for processing fluid passed through the processor, in which the switching means includes first switching means on the fluid in-flow space side and second switching means on the fluid out-flow space side, and which comprises a first step of rendering the first on-off means to be in a closed state, a second step of rendering the second on-off means to be in an open state and switching the first switching means to the first pressure supply flow path and switching the second switching means to be first pressure supply flow path, a third step of rendering the second on-off means to be closed state, a fourth step of rendering the first on-off means to be in an open state, a fifth step of switching the first switching means to be second pressure supply flow path and a sixth step of switching the second switching means to the second pressure supply flow path, these steps being sequentially and repeatedly executed.

According to the invention, there is further provided a method of driving an apparatus for processing fluid, which further comprises a step of blocking both the flow paths with the first switching means and a step of blocking both the flow paths with the second switching means after the second step and before the third step, a step of blocking both the flow paths with the first switching means and a step of blocking both the flow paths with the second switching means after the sixth step and before the first step.

In this method, with the first step of rendering the first on-off means to be in an open state and second step of rendering the second on-off means to be in an open state and switching the first switching means to the first pressure supply flow path and switching the second switching means to the first pressure supply flow path fluid in the fluid out-flow space is led out through the fluid port, while fluid in the fluid in-flow space is forced through the fluid processor into the fluid out-flow space, and with the third step of rendering the second on-off means to be in a closed state and fourth step of rendering the first on-off means to be in an open state, fifth step of switching the first switching means to the second pressure supply flow path and sixth step of switching the second switching means to the second pressure supply flow path fluid is introduced through the fluid in-flow space through the fluid port, while fluid in the fluid in-flow space is forced through the fluid processor into the fluid in-flow space.

Further, according to the invention there is provided an apparatus for processing fluid, which comprises first communicating/blocking means for communicating and blocking the first pressure supply flow path and second communicating/blocking means for communicating and blocking the second pressure supply flow path, and in which an in-flow side flexible member is operated, which comprises a first step of rendering the first on-off means to be in a closed state, a second step of blocking the second communicating/blocking means after the first step, a third step of rendering the second on-off means to be in an open state after the second step, a fourth step of communicating the first communicating/blocking means after the third step, a fifth step of substantially simultaneously rendering the second on-off means to be in a closed state, blocking the first communicating/blocking means and communicating the second communicating/blocking means after the fourth step and a sixth step of rendering the first on-off means to be in an open state after the fifth step, these steps being executed sequentially and repeatedly.

By executing these steps sequentially and repeatedly, fluid can be caused to flow more smoothly from the fluid port of the fluid in-flow space to the fluid out-flow space, and it is possible to prevent stagnation of fluid in the fluid in- and out-flow spaces.

Further with the step of blocking both the flow paths with the switching means it is possible to prevent excessive increase of the pressure of blood in the oxygenator or reduction of pressure (to negative pressure), and it is possible to prevent stagnation and reverse flow more satisfactorily. These effects may be further improved with a step of blocking both the flow paths with the first and second communicating/blocking means and a step of reliably performing the operation of the port on-off means and first and second communicating/clocking means.

DESCRIPTION OF THE PREFERRED EMBODIMENT

Now, an embodiment of the invention will be described with reference to the accompanying drawings.

Figure 1:
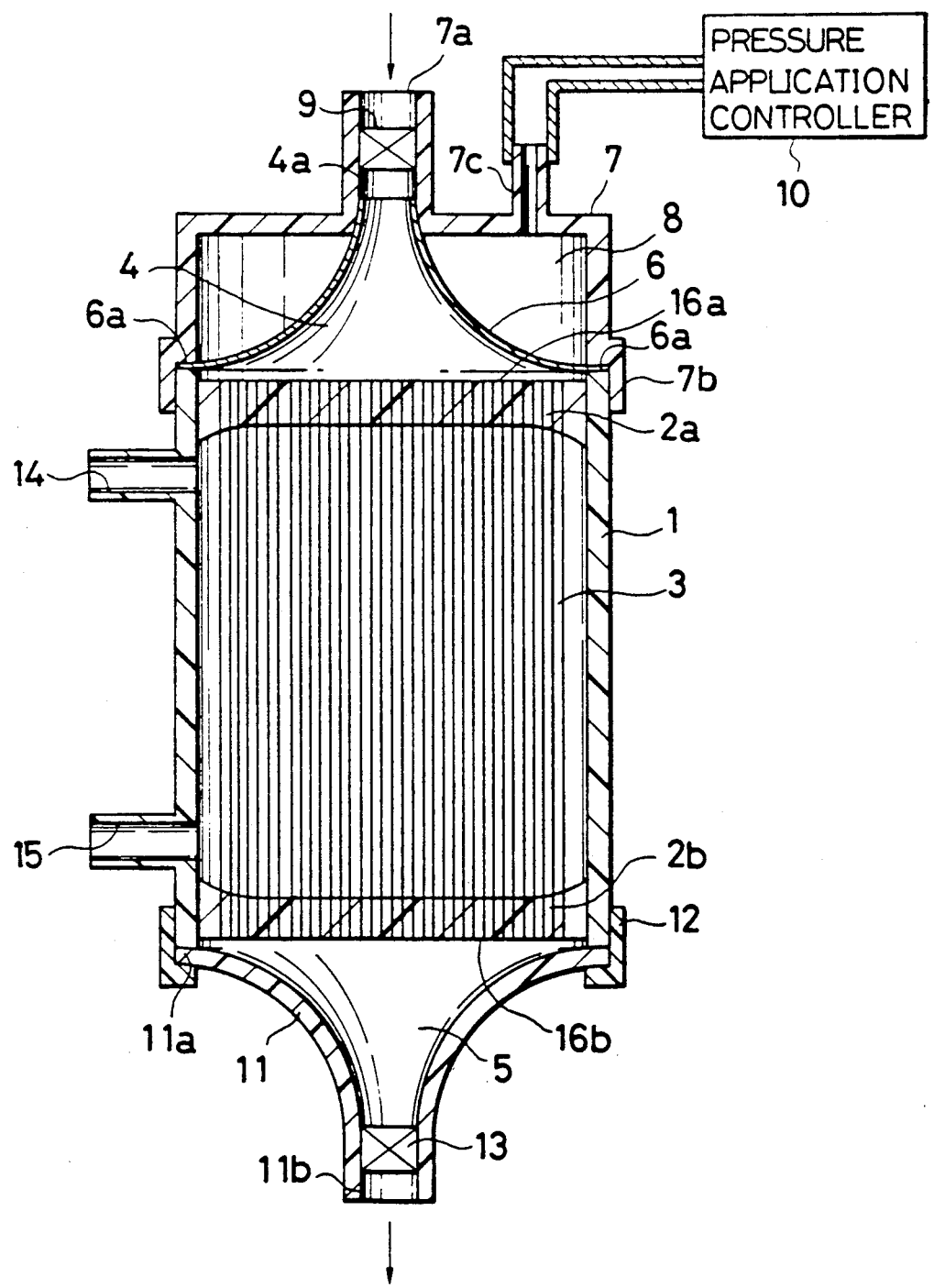
FIG. 1 is a sectional view showing a first embodiment of the invention applied to a hollow fiber type oxygenator.

FIG. 1 is a sectional view showing a hollow fiber type oxygenator as first embodiment of the invention. Referring to the drawings, reference numeral 1 designates cylindrical housing surrounding the periphery of a blood processor, in which gas exchange between carbon dioxide in blood and oxygen takes place. Housing 1 accommodates hollow fiber bundle 3 consisting of hollow fibers serving as gas exchange membrane. The hollow fibers are usually porous, but in this embodiment diffusion membrane is suitably used. With the diffusion membrane, unlike porous hollow fiber, the inner and outer sides are not in direct communication with each other. Therefore, even in the event of generation of negative pressure in the circuit, with the diffusion membrane there is no possibility of introduction of bubbles into blood or rupture of blood cells. The diffusion membrane can be obtained by filling the pores of porous hollow fibers with silicone resin (RTV), for instance.

The opposite ends of hollow fiber bundle 3 are supported liquid-tight by partitioning walls 2a and 2b, made of a polyurethane resin, for instance, such that the open ends of the hollow fibers are exposed to form blood inlet 16a and blood outlet 16b. The blood processor noted above is constituted in this way. Adjacent to the opposite ends of hollow fiber bundle 3, blood inlet and outlet spaces 4 and 5 are provided such that they communicate with blood inlet 16a and blood outlet 16b, respectively. Conical flexible member 6 is disposed such as to face partitioning wall 2a and has opening 4a formed at an end. Blood in-flow space 4 is defined between flexible member 6 and partitioning wall 2a. Flexible member 6 consists of a silicone resin membrane, for instance, and is capable of being deformed by fluid pressure to be described later for reciprocal operation toward and away from partitioning member 2a. Flexible member 6 has its edge 6a secured to the edge of the upper end of housing 1. Outside flexible member 6, operation chamber forming member 7 is provided. Operation chamber forming member 7 has central blood inlet 7a, and operation chamber 8 is defined between operation chamber forming member 7 and flexible member 6. Operation chamber forming member 7 is fitted on an end portion of housing 1 and held in close contact with the edge of flexible member 6 by rim 7b provided at its open end. Open end 4a of flexible member 6 is secured to and communicated with blood inlet 7a provided on operation chamber forming member 7. Check valve 9 is provided in blood inlet 7a. It blocks flow of blood from blood in-flow space 4 through blood inlet 7a while it permits flow of blood into space 4. Operation chamber forming member 7 is provided with fluid pressure supply port 7c. Fluid pressure supply means, for instance pressure application controller 10, is coupled to fluid pressure supply means to provide fluid pressure for reciprocally operating flexible member 6 in operation chamber 8.

Pressure application controller 10 can freely control the pressure application state in operation chamber forming member 7. It may include an electromagnetic valve, which on-off controls supply of compressor air produced inside or outside the system to pressure application controller 10, an electromagnetic valve for on-off controlling the releasing of pressure applied to pressure application controller 10 to atmosphere and a control unit for controlling the timings of operation of these electromagnetic valves. It may be light in weight, small in size and readily manufactured compared to the prior art oxygenator roller pump.

Conical header 11 has its edge 11a secured by bonding to the end of housing 1, with other partitioning member 2b secured thereto. Blood outlet space 5 noted above is defined between header 11 and partitioning member 2b. Annular member 12 is secured to the outer periphery of end portion 11a of header 11, to which partitioning member 2b is bonded, for reinforcing the securement of header 11 and housing 1 to each other. The center of an end of header 11 is provided with blood outlet 11b. In blood outlet 11b is disposed check valve 13 which constitutes together with check valve 9 noted above port on-off means for reverse flow prevention. Check valve 13 blocks flow of blood into blood out-flow space 5 through blood outlet 11b while it permits flow of blood out of space 5. Reference numeral 15 oxygen-containing gas inlet, and 14 gas outlet for gas after gas exchange.

In this example of hollow fiber oxygenator having the above construction, with gas or liquid introduced from pressure application controller 10 through fluid pressure supply port 7c into operation chamber 8, flexible member 6 is reciprocated by the fluid pressure. The reciprocation of flexible member 6 causes pressure variations of blood in blood-flow space 4. With this pressure variation and also with the function of two check valves 9 and 13, blood introduced through blood inlet 7a flows smoothly through hollow fiber bundle 3 from the side of blood in-flow space 4 to the side of blood out-flow space 5, as shown by arrows in the Figure, and during this flow gas exchange is effected with oxygen-containing gas introduced from gas inlet 14.

In this embodiment of hollow fiber type oxygenator, the pump is accommodated in the apparatus body, and separate roller pump for blood supply is not necessary. This means that there is no need of connecting apparatus body and pump with tubing for assembling the system as in the prior art, and the assembling can be readily performed. In the case of the roller pump, the tube of which is squeezed from the outside to push out blood, a circuit is set by connecting together various components with tubes and is thereafter fitted in a roller portion of the roller pump. That is, the circuit has to be assembled before being set in the roller pump. In contrast, with this embodiment of oxygenator, the assembling of the circuit and connection thereof to pressure application controller 10 are performed concurrently, which is convenient for operation. In addition, the area of installation of the system can be reduced compared to the prior art case.

Further, since no roller pump is required for blood supply, the volume of priming can be reduced by the volume of tube portion set in the roller pump (usually this tube portion having an increased diameter to obtain a predetermined flow). Still further, there is no problem of leakage or contamination of blood due to otherwise possible generation of cracks in tubes.

Further, since blood is introduced with reciprocal operation of flexible member 6, blood never becomes stagnant in blood in-flow space 4. Thus, there is no possibility of generation of thrombus and resultant clogging of the apparatus.

Figure 2:
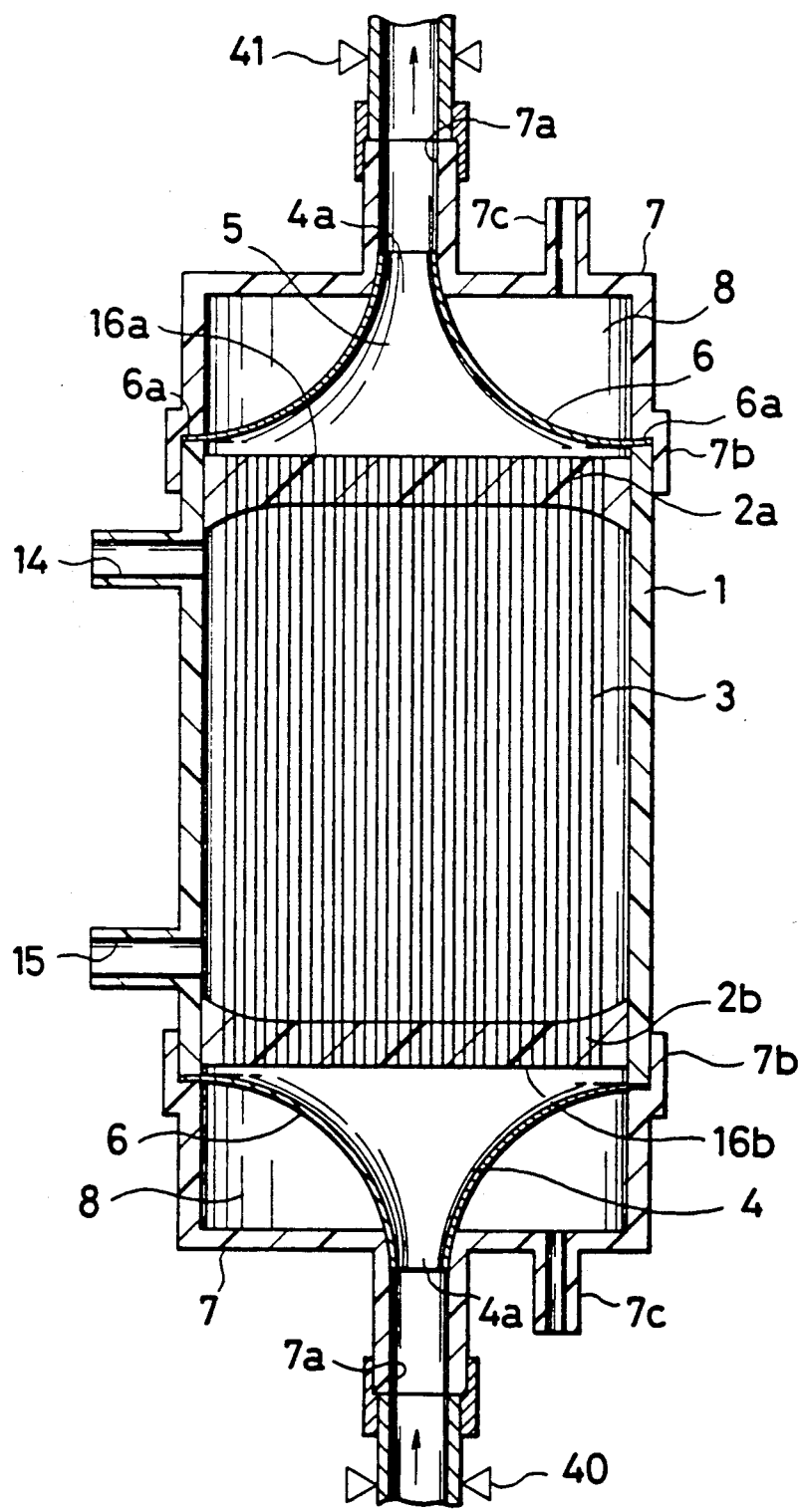
FIG. 2 is a sectional view showing a hollow fiber type oxygenator as second embodiment of the invention.
Figure 3:
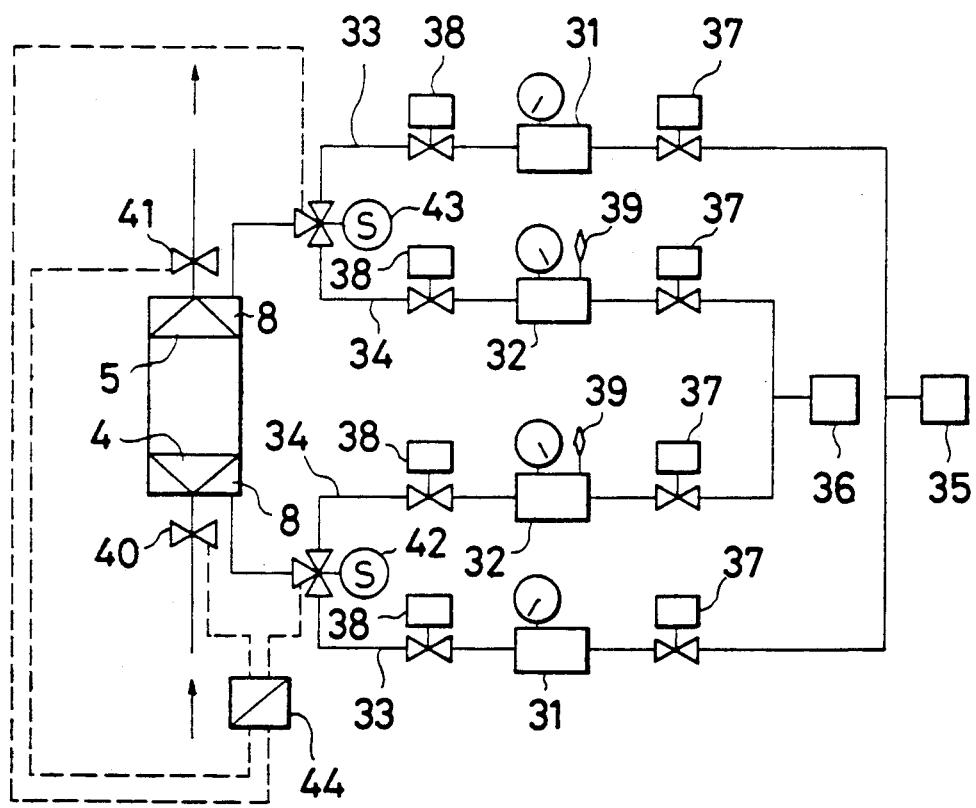
FIG. 3 is a view showing a driver circuit for the same oxygenator.

FIG. 2 shows a hollow fiber type oxygenator as second embodiment of the invention, and FIG. 3 shows a driver circuit of the oxygenator. With this oxygenator, the in-flow side of blood processor has the same construction as the out-flow side of the blood processor in the preceding first embodiment. That is, flexible member 6 and operation chamber 8 are provided in each of the in- and out-flow sides. In FIG. 2, parts like those in FIG. 1 are designated by like reference numerals, and their description here is omitted.

In this embodiment of oxygenator, blood is caused to flow upwardly through the blood processor. Where blood is caused to flow conversely, i.e., downwardly, when operation chamber 8 is communicated with a positive pressure source, blood in-flow side clamp is held open, while blood in-flow side clamp is held closed. When the operation chamber is communicated with a negative pressure source (or atmosphere), on the other hand, the out-flow side clamp is held closed while holding the in-flow side clamp open. With such arrangement, blood can smoothly flows in and out owing to pressure due to head. Thus status can be suitably used for a V-V bypass.

In the oxygenator of this embodiment, the port on-off means includes first on-off means, for instance clamp 40, provided on a tube connected to blood port 7a of blood in-flow space 4 and second on-off means, for instance clamp 41, provided on a tube connected to blood port 7a of blood out-flow space 5. With the port on-off means constituted by clamps 40 and 41 in this way, satisfactory effects can be obtained by prevention of thrombus.

In this case, the tube that is clamped suitably is one with an outer diameter of 5 to 14 mm.

It is possible to replace clampes 40 and 41 as first and second port on-off means with electromagnetic valves or the like.

The fluid pressure supply means includes positive pressure tank 31 with confirmation gauge (of 0 to 1.0 kg/cm$^2$) as first pressure source for providing a positive fluid pressure to operation chamber 8, air compressor 35 for the positive pressure tank, negative pressure tank 32 with confirmation gauge ($-0.5$ kg/cm$^2$ to atmospheric pressure) as second pressure source for providing negative fluid pressure of atmospheric pressure to operation chamber 8, vacuum pump 36 for negative pressure tank 32, positive pressure supply flow path 33 as first pressure supply flow path connecting positive pressure tank 31 and operation chamber 8, negative/atomospheric supply flow path 34 as second pressure supply flow path connecting negative pressure tank 32 and operation chamber 8 and three-way electromagnetic valves 42 and 43 as switching means for repeatedly switching the two flow paths. In lieu of the switching means, electromagnetic valves may be provided on positive and negative/atmospheric pressure supply flow paths 33 and 34 and on-off operated to switch the flow paths.

Vacuum pump 36 is suitably of diaphragm type capable of operation for long time rather than oil rotation type in view of accuracy, and also it can sufficiently withstand driving at 30 to 40 rotations/min. (50 ml/rotation). Negative pressure tank 32 includes leak valve 39 for communication to atmosphere. By opening this valve, atmospheric pressure can be provided. Pressure regulator valves 37 are provided between air compressor 35 and positive pressure tank 31 and also between vacuum pump 36 and negative pressure tank 32, for effecting master pressure adjustment of the individual tanks. Flow control valves 38 are provided between electromagnetic valves 42 and 43 on one hand and positive and negative pressure tanks 31 and 32 on the other hand. Flow control valves 38 suitably are capable of fine adjustment at low flow rate (of 0.5 to 10 l/min.), and their maximum flow is suitably about several ten l/min.

Three-way electromagnetic valve 42 constitutes first switching means and is connected to fluid pressure supply port 7c of operation chamber 8 of blood in-flow space 4, and three-way electromagnetic valve 43 constitutes second switching means and is connected to fluid pressure supply port 7c of operation chamber 8 of blood out-flow space 5.

Tubes forming positive and negative/atmospheric pressure supply flow paths 33 and 34 in the circuit noted above suitably are pressure-resistant vinyl chloride tubes with inner diameter of about 5 mm.

In this oxygenator, the operations of clamps 40 and 41 and electromagnetic valves 42 and 43 are controlled by controller 44 constituting control means. The port on-off means, which includes clamps 40 and 41 and electromagnetic valves 42 and 43, and fluid pressure supply means constitute a driver for causing circulation of blood through the blood processor.

The driver can be controlled in various modes to be described hereinafter.

Mode 1

Figure 4:
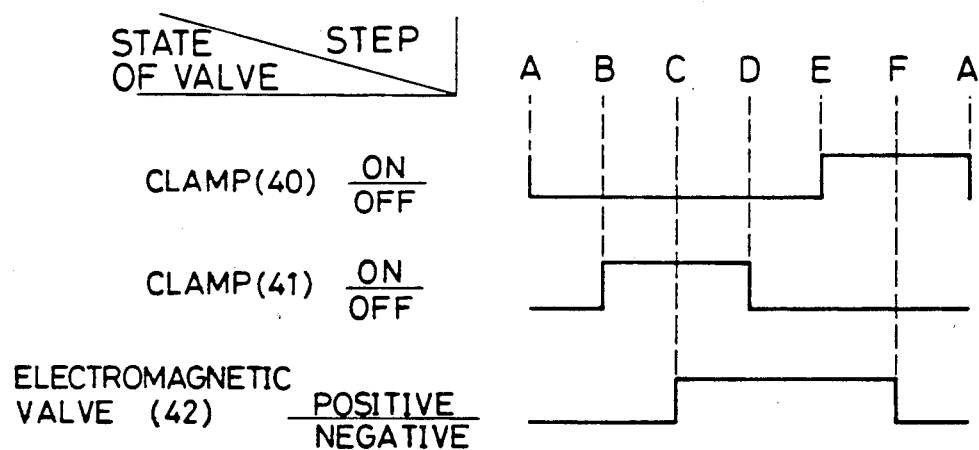
FIG. 4 is a view for explaining operation in mode 1.
Figure 5:
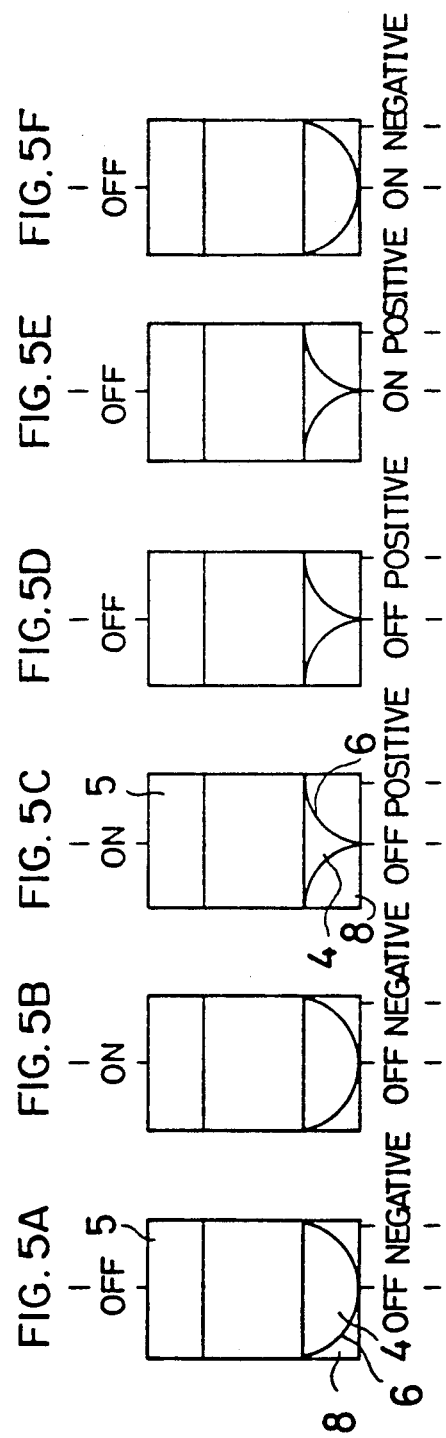
FIG. 5 is a view illustrating operational states of a flexible member in mode 1.

In this mode of control, only flexible member 6 in in-flow side operation chamber 8 is operated without operation of flexible member 6 in out-flow side operation chamber 8. FIG. 4 (A to F) illustrates steps of operation of the individual clamps and electromagnetic valves, and FIG. 5 (A to F) schematically illustrates operational states of in-flow side flexible member 6 in individual steps.

In step A, clamp 40 is closed. In this step, clamp 41 is closed, and electromagnetic valve 42 is in communication with negative pressure supply flow path 34. Thus, a negative pressure or atmospheric pressure is provided in operation chamber 8, and flexible member 6 is withdrawn.

By subsequently opening clamp 41 (step B) and then switching electromagnetic valve 42 to the side of positive pressure supply flow path 33 (step C), a positive fluid pressure is set up in operation chamber 8, and flexible member 6 is urged by this positive pressure. As a result, the pressure in blood in blood in-flow space 4 is increased. Thus, blood is forced through the blood processor into blood out-flow space 5, and thence is led out through blood port 7a. The closure of clamp 41 and switching of electromagnetic valve 42 may be effected simultaneously or conversely. Further, the closure of clamp 40, closure of clamp 41 and switching of electromagnetic valve 42 may be effected simultaneously.

Subsequently, by closing clamp 41 (step D), opening clamp 40 (step E) and switching electromagnetic valve 42 to the side of negative/atmospheric pressure supply flow path 34 (step F), a negative or atmospheric pressure is provided in operation chamber 8. In consequence, flexible member 6 is restored to the initial state (withdrawn state) (step F). Thus, pressure in blood in blood in-flow space 4 is reduced to cause blood to be introduced into blood in-flow space 4.

Of steps D to F, steps D and E, steps E and F or steps D to F may be executed substantially simultaneously.

Then the routine goes back to step A to repeatedly execute the individual steps.

The individual steps are desirably adjusted with a unit of 0.1 sec. and in 2.0 sec. for proceeding to the next step. Steps C and F, however, are desirably adjusted with a unit of 0.1 sec. and in 30 sec. for proceeding to the next step.

Mode 2

Figure 6:
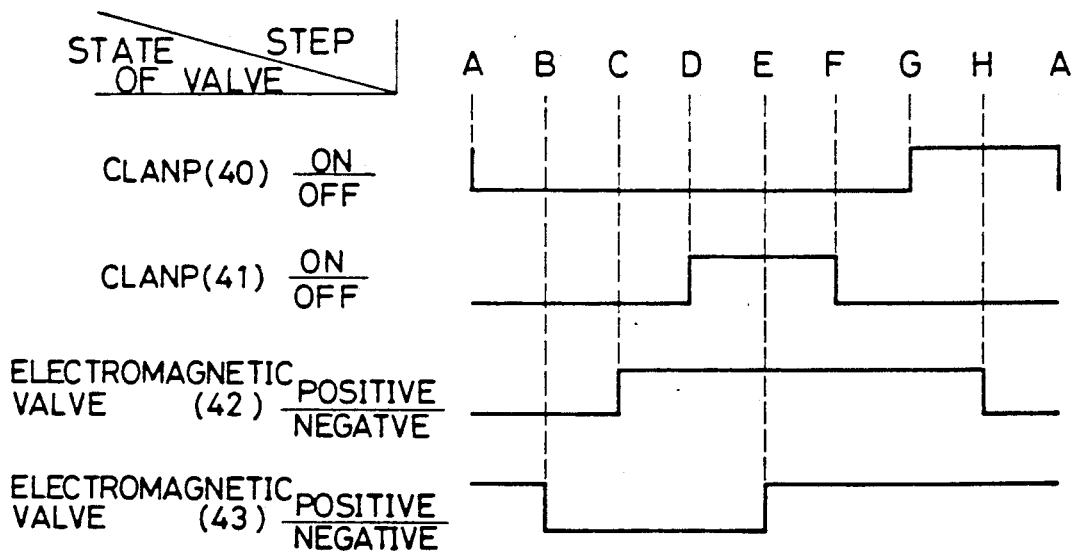
FIG. 6 is a view for explaining operation of mode 2.
Figure 7:
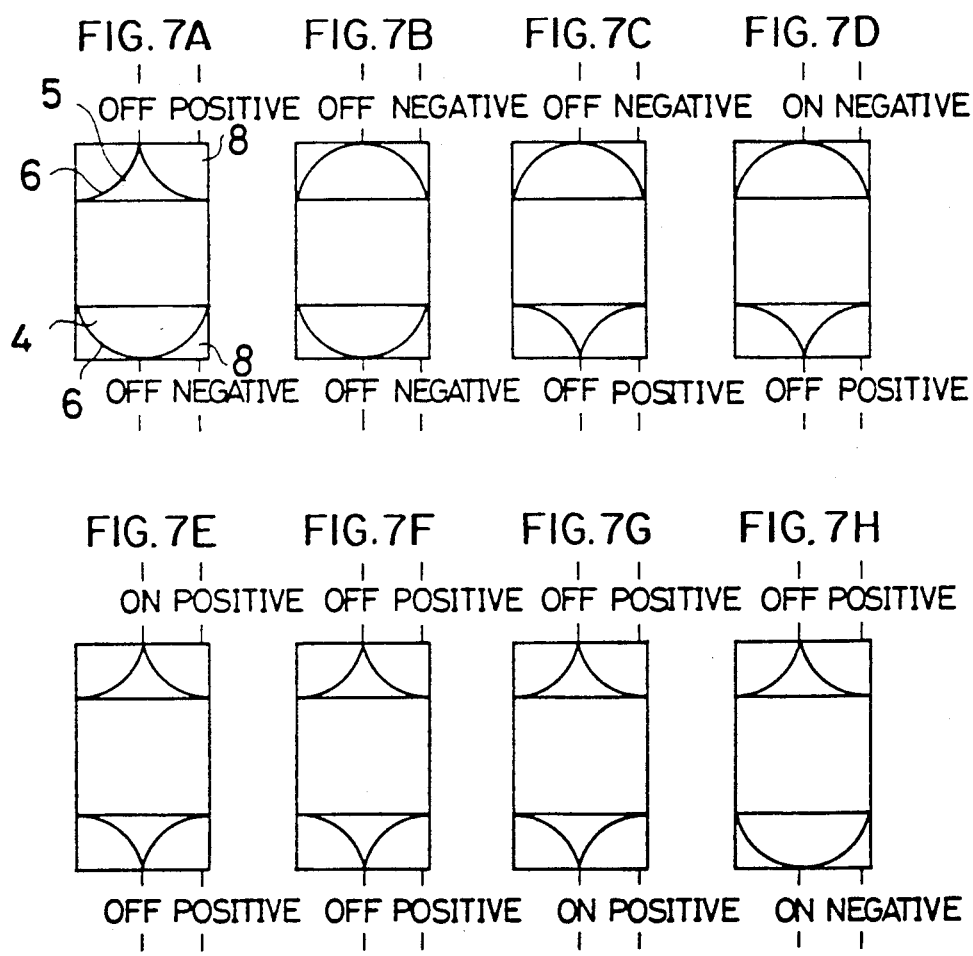
FIG. 7 is a view illustrating operational states of flexible member in mode 2.

In this mode of control, flexible members 6 in both in- and out-flow side operation chambers 8 are operated. FIG. 6 (A to H) illustrates steps of operation of the individual clamps and electromagnetic valves, and FIG. 7 (A to H) illustrates operational states of flexible members 6 in the individual steps.

First, in step A clamp 40 is closed. At this time, clamp 41 is in closed state, electromagnetic valve 42 is in communication with negative/atmospheric pressure supply flow path 34, and electromagnetic valve 43 is in communication with positive pressure supply flow path 33. In this state, negative or atmospheric pressure prevails in in-flow side operation chamber 8, and positive pressure prevails in out-flow side operation chamber 8. Thus, in-flow side flexible member 6 is in a pulled state, and out-flow side flexible member 6 is in a pushed state.

Subsequently, by switching electromagnetic valve 43 to the side of negative/atmospheric pressure supply flow path 34 (step B) and switching electromagnetic valve 42 to positive pressure supply flow path 33 (step C), negative or atmospheric pressure is set up in out-flow side operation chamber 8, and positive pressure is set up in in-flow side operation chamber 8. Thus, out-flow side flexible member 6 is pulled, and in-flow side flexible member 6 is pushed. Blood in blood in-flow space 4 is thus forced through the blood processor into blood out-flow space 5. The switching of electromagnetic valve 43 and switching of electromagnetic valve 42 may be effected simultaneously or conversely.

Subsequently, by opening clamp 41 (step D) and switching electromagnetic valve 43 to the side of positive pressure supply flow path 33 (step E), in-flow side flexible member 6 is pushed, and out-flow side flexible member 6 is pushed. Blood in blood out-flow side space 5 is thus led out through the blood port. The opening of clamp 41 and switching of electromagnetic valve 43 may be effected simultaneously or conversely.

Subsequently, by closing clamp 41 (step F), opening clamp 40 (step G) and switching electromagnetic valve 42 to the side of negative/atmospheric pressure supply flow path 34 (step H), negative or atmospheric pressure is set up in-flow side operation chamber 8. Thus, in-flow side flexible member 6 is pulled to permit blood to be introduced into blood in-flow space 4 (step H).

Of steps F to H, steps F and G, steps G and H or steps F to H may be executed substantially simultaneously.

Then the routine goes back to step A to repeatedly execute the individual steps.

The individual steps are desirably adjusted with a unit of 0.1 sec. and in 2.0 sec. for proceeding to the next step. Steps C, E and H, however, are desirably adjusted with a unit of 0.1 sec. and in 30 sec. for proceeding to the next step.

Mode 3

Figure 8:
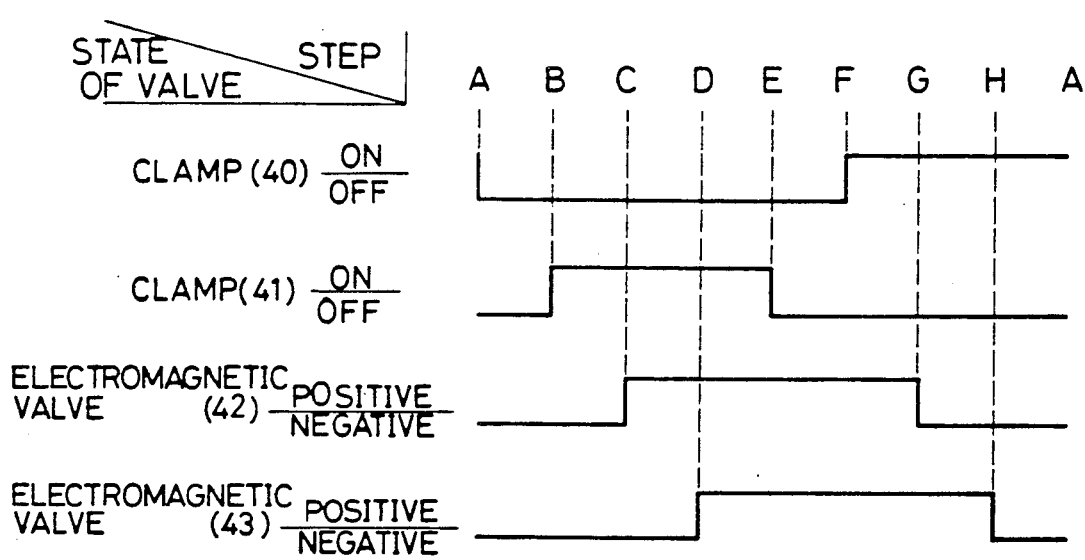
FIG. 8 is a view for explaining operation in mode 3.
Figure 9:
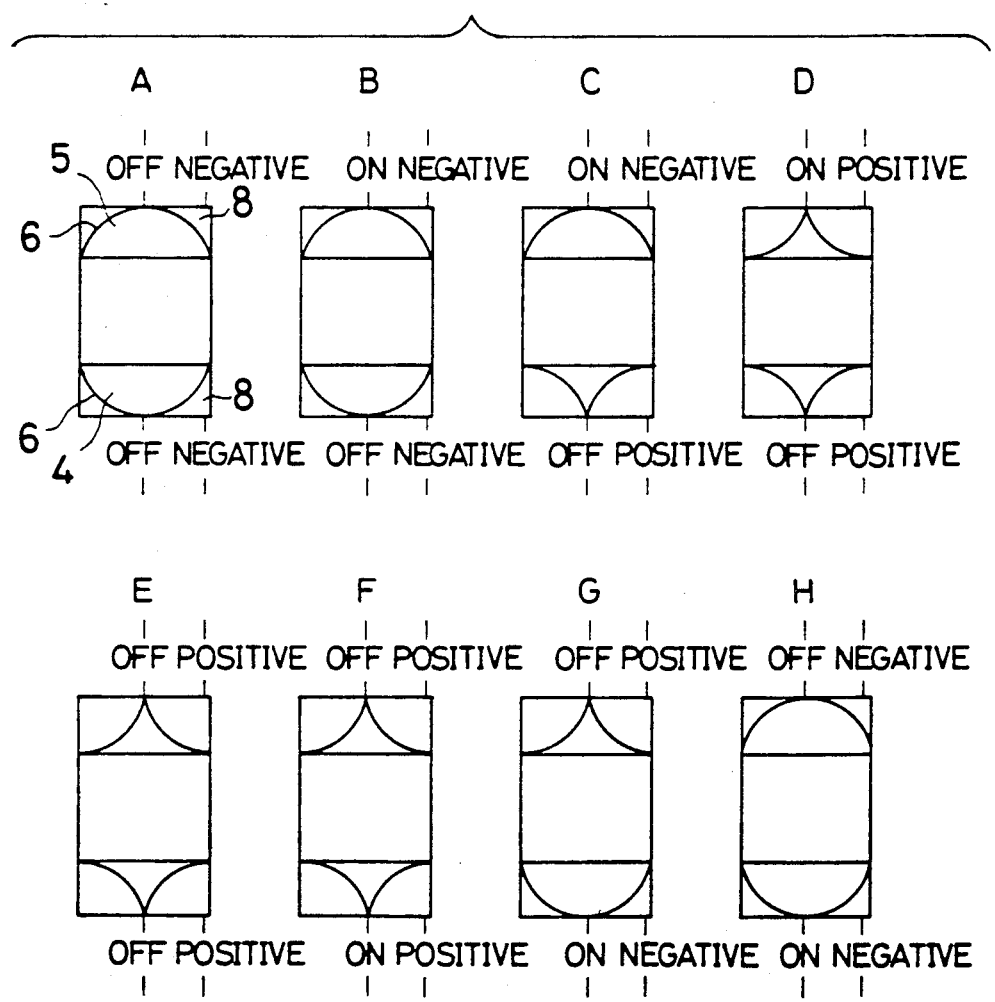
FIG. 9 is a view illustrating operational states of flexible member in mode 3.

In this mode of control, like mode 2, in- and out-flow side flexible members 6 are both operated. FIGS. 8 (A to H) illustrate steps of operation of the individual clamps and electromagnetic valves, and FIG. 9 (A to H) illustrates operational states of the flexible members in the individual steps.

First, in step A clamp 40 is closed. At this time, clamp 41 is in closed state, and electromagnetic valves 42 and 43 are in communication with negative/atmospheric pressure supply flow path 34.

Subsequently, by opening clamp 41 (step B), switching electromagnetic valve 42 to the side of positive pressure supply flow path 33 (step C) and switching electromagnetic valve 42 (step C) and switching electromagnetic valve 43 to the side of positive pressure supply flow path 33, positive pressure is set up in both in- and out-flow side operation chambers 8. Thus, both in- and out-flow side flexible members 6 are pushed. Blood in blood out-flow space 4 thus is forced out through the blood processor into blood out-flow space 5, and thence through blood port 7a to the outside.

Of the individual steps, steps A and B, steps B and C, steps C and D, steps A to C, steps B to D and steps A to D may be executed substantially simultaneously. It is further possible to execute steps C, D and B in the mentioned order subsequent to step A.

Subsequently, by closing clamp 41 (step E), then opening clamp 40 (step F) and then switching electromagnetic valve 42 to the side of negative/atmospheric pressure supply flow path 34 (step G), negative or atmospheric pressure is set up in in-flow side operation chamber 8. Thus, in-flow side flexible member 6 is pulled to permit blood to be introduced into blood in-flow space 4.

Subsequently, by switching electromagnetic valve 43 to the side of negative/atmospheric pressure supply flow path 34 (step H), negative or atmospheric pressure is set up in out-flow side operation chamber 8. Thus, blood in the blood processor is forced into blood out-flow space 5 into the blood processor and thence into blood in-flow space 4.

In the individual steps, steps E and F, steps F and G, steps G and H, steps E to G, steps F to H or steps E to H may be executed substantially simultaneously.

The individual steps as in mode 1 are desirably adjusted with a unit of 0.1 sec. and in 2.0 sec. for proceeding to the next step. Steps C, D, G and H, however, are desirably adjusted with a unit of 0.1 sec. and in 30 sec. for proceeding to the next step.

Mode 4

Figure 10:
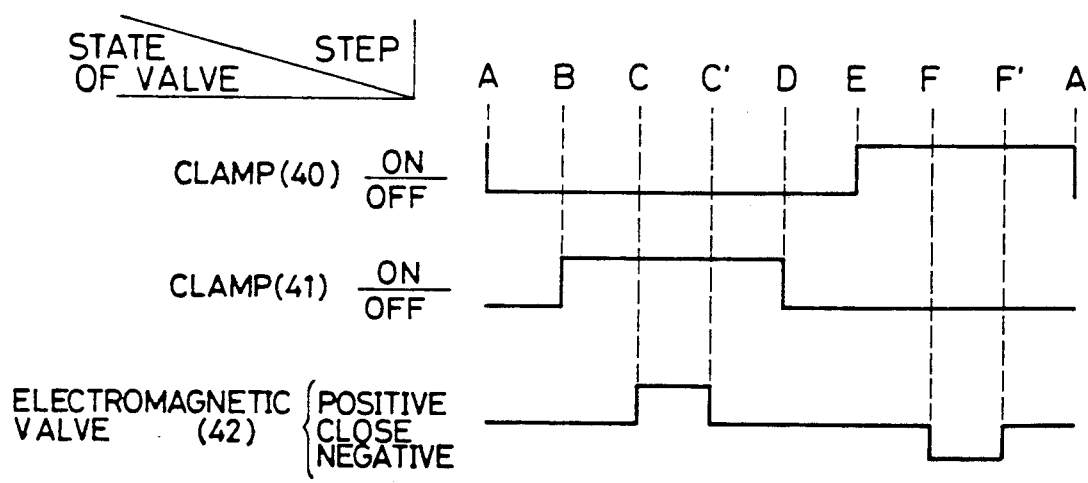
FIGS. 10 to 12 are views for explaining operation in modes 4 to 6.

This mode of control, as shown in FIG. 10, is obtained by adding step C' between steps C and D and step F' between steps F and A in mode 1.

More specifically, in step C' after step C both positive and negative/atmospheric pressure supply flow paths 33 and 34 are blocked, and then step D is executed.

While in step C positive pressure is set up in operation chamber 8 to force blood from blood in-flow space 4 into blood out-flow space 5, if clamp 41 is closed during this operation, blood can no longer be let out through the blood port, that is, it is liable that blood can find no place to go to, in spite of the positive pressure in operation chamber 8. Accordingly, prior to step D of closing electromagnetic valve 43, both the flow paths are blocked by electromagnetic valve 42 so neither positive nor negative pressure is subsequently set up in operation chamber 8 and that the above liability is reliably eliminated.

Regarding step F', if clamp 40 is closed in the presence of negative pressure in operation chamber 8, negative pressure is produced in the hollow fibers. In this case, external air is liable to be introduced into the hollow fibers if the hollow fibers are microporous. For this reason, in step F' both the flow paths are blocked, and subsequently step A is executed.

The remainder of operation is the same as in mode 1, so it is described no further.

In FIG. 10 notation "close" as valve state means that both positive and negative/atmospheric pressure supply flow paths 33 and 34 are blocked. The same meaning holds in FIGS. 11 and 12.

Mode 5

Figure 11:
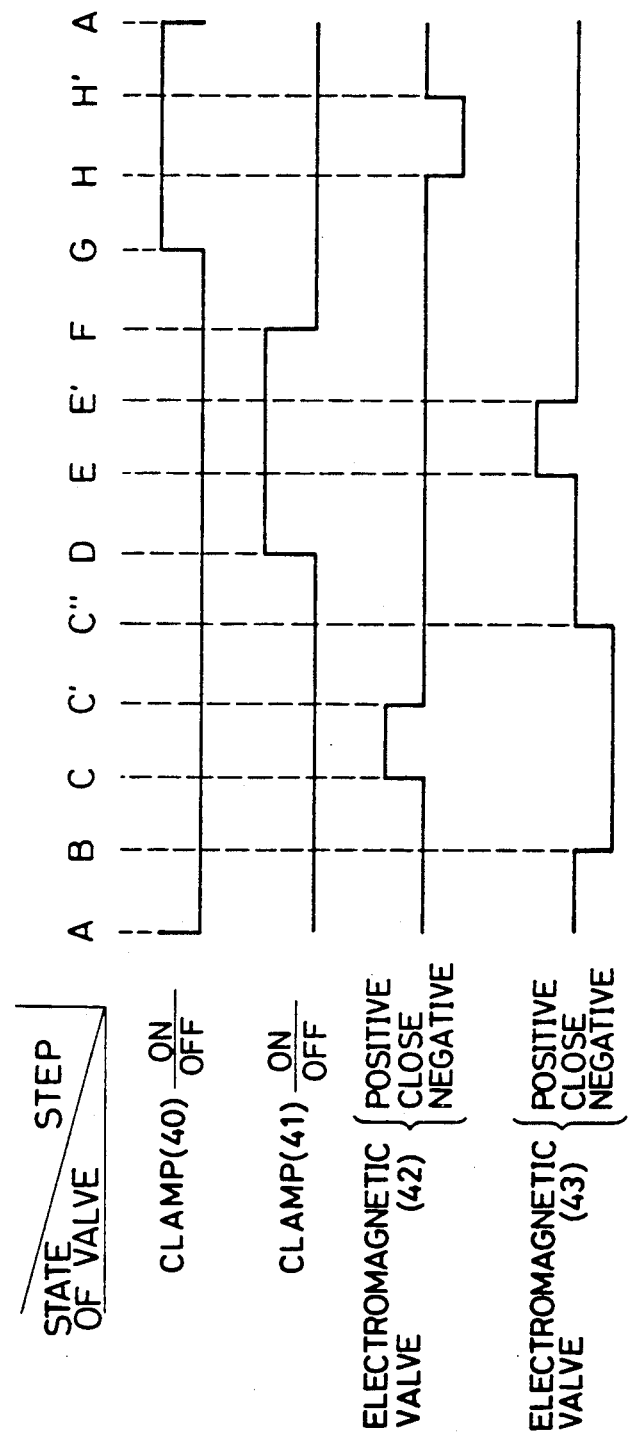

This mode of control, as shown in FIG. 11, is obtained by adding steps C' and C" after step C and before step D, step E' after step E and before step F and step H' after step H and before step A in mode 2.

Both positive and negative/atmospheric pressure supply flow paths 33 and 34 are blocked by operating electromagnetic valve 42 in step C', electromagnetic valve 43 in step C", electromagnetic valve 43 in step E' and electromagnetic valve 42 in step H'. In this way, excessive pressure rise or pressure fall (generation of negative pressure) in the oxygenator is eliminated to eliminate the undesired possibility as discussed before in connection with mode 4.

Mode 6

Figure 12:
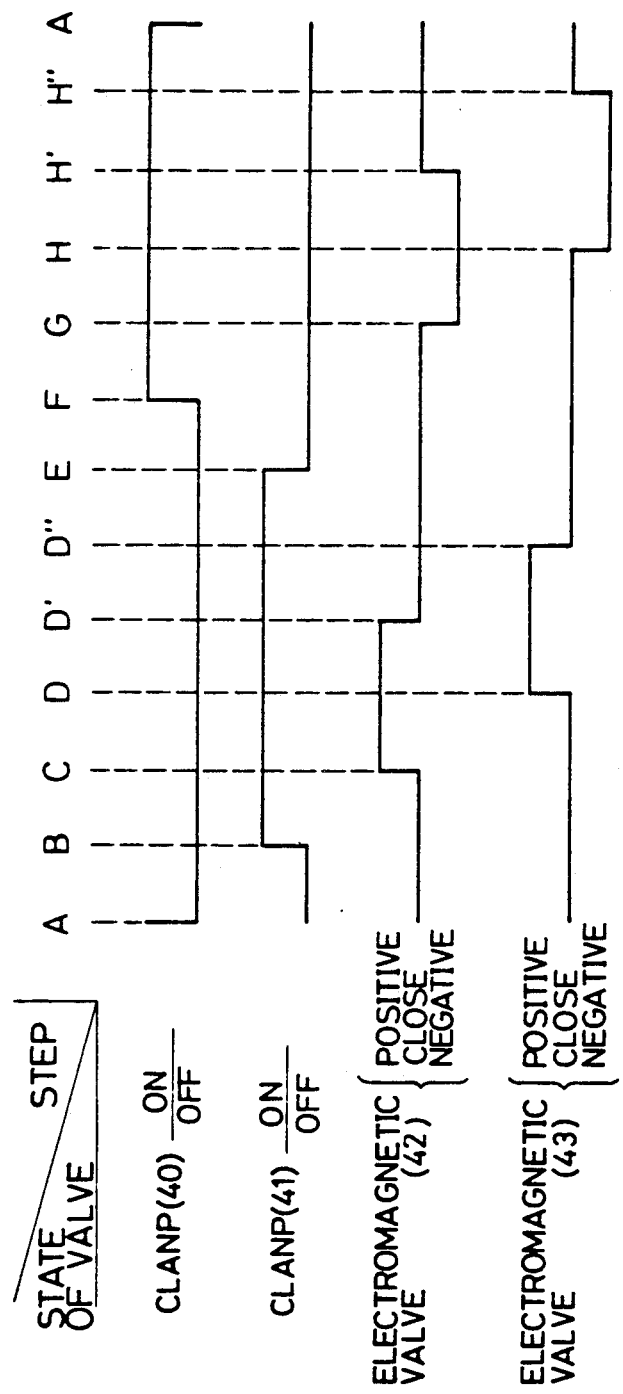

This mode of control, as shown in FIG. 12, is obtained by adding steps D' and D" after step D and before step E and steps H' and H" after step H and before step A in mode 3.

Both positive and negative/atmospheric pressure supply flow paths 33 and 34 are blocked by operating electromagnetic valve 42 in step D', electromagnetic valve 43 in step D", electromagnetic valve 42 in step H' and electromagnetic valve 43 in step H", thus eliminating the possibility as discussed before in connection with mode 4.

The remainder of operation is the same as in mode 3.

In modes 1 to 6 described above, the individual steps are sequentially repeated, thus enhancing the smoothness of blood flow from blood port 7a of blood in-flow space 4 through the blood processor to blood port 7a of blood out-flow space 5. In this way, it is possible to effectively prevent stagnation of blood in blood in- and out-flow spaces 4 and 5.

Figure 13:
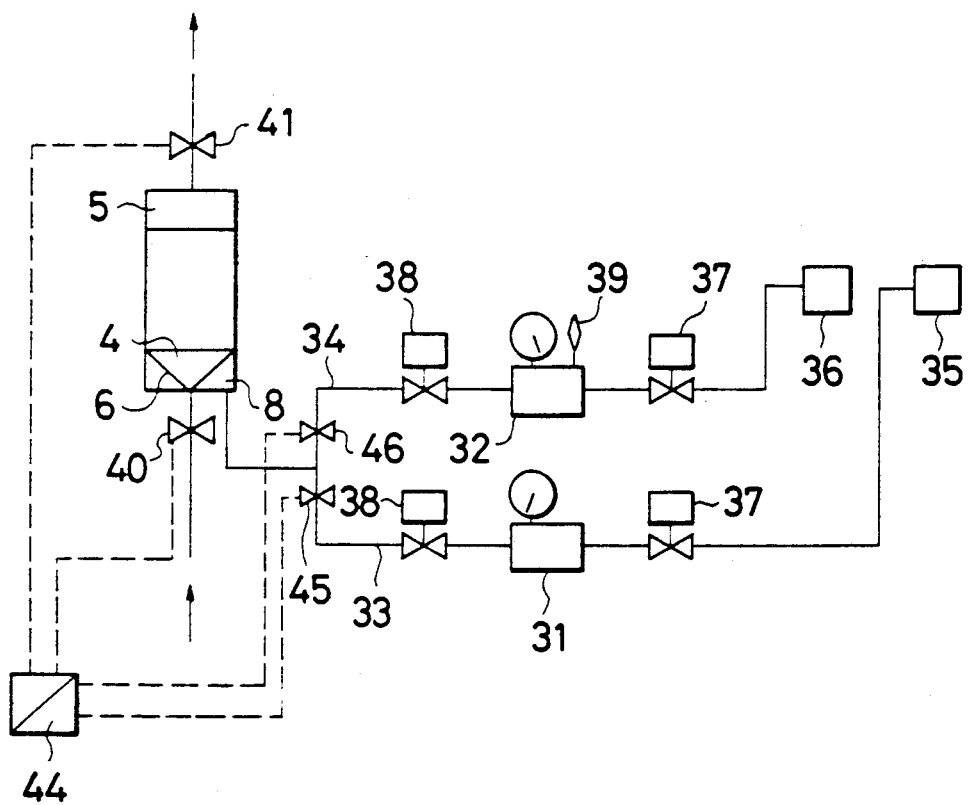
FIG. 13 is a view showing a driver circuit of a hollow fiber type oxygenator as third embodiment of the invention.

FIG. 13 shows a driver circuit of a hollow fiber type oxygenator as third embodiment of the invention. This oxygenator operates only flexible member 6 on the in-flow side of blood processor. In fluid pressure supply means, first pressure supply flow path 33 communicating positive pressure tank 31 and operation chamber 8 is provided with electromagnetic valve 45 constituting first communicating/blocking means for communicating and blocking the flow path, and second pressure supply flow path 34 communicating negative pressure tank 32 and operation chamber 8 is provided with electromagnetic valve 46 constituting second communicating/blocking means for communicating and blocking the flow path. Electromagnetic valves 45 and 46 constitute switching means. In FIG. 13, parts like those in the proceeding second embodiment are designated by like reference numerals, and its description is omitted.

With the oxygenator having this construction, the port on-off means and fluid pressure supply means can be driven in mode 7 to be described later.

Mode 7

Figure 14:
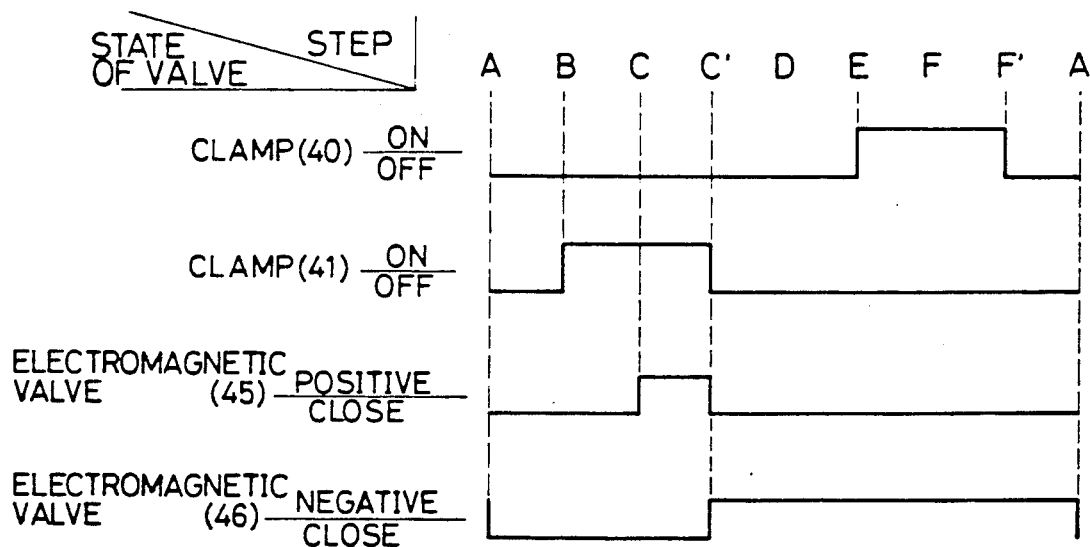
FIG. 14 is a view for explaining operation in mode 7.

This mode of control is based on mode 4 as shown in FIG. 14.

Subsequent to step F' of closing clamp 40, after lapse of time necessary for completion of closing of clamp 40, for instance 0.2 sec., electromagnetic valve 46 is blocked (step A), then subsequent to step A clamp 41 is opened after lapse of time necessary for completion of blocking operation of electromagnetic valve 46, for instance 0.1 sec. (step B), and further subsequent to step B electromagnetic valve 45 is opened for communication after lapse of time necessary for completion of opening of clamp 40, for instance 0.1 sec. (step C). In this way, in step C clamps 40 and 41 and electromagnetic valves 45 and 46 assume the same states as in step C in mode 4.

Subsequently, clamp 41 is closed and electromagnetic valve 46 is opened substantially simultaneously with blocking of electromagnetic valve 45 (step C'), and clamp 40 is opened in the time necessary for a change in the status of tubes constituting flow paths 33 and operation chamber 8 from positive pressure state to negative pressure state, for instance after lapse of time, 0.2 sec. (step E).

In this mode 7, the timings of operation of clamps 40 and 41 and electromagnetic valves 45 and 46 may be shifted to permit the routine to go to the next step after completion of the individual operations for avoiding sharp peak blood pressure in the oxygenator. It is further possible to improve the function and effects described before in mode 4. Mode 7 can be executed by operating the sole in-flow side flexible member, and thus it permits the structure of the oxygenator to be simplified. It is desirable that the above shifting in timing is set in accordance with volume compliance of the tube and switching speed of the cylinder. Where the hollow fibers have diffusion membranes, the pressure provided from the negative pressure source to operation chamber 8 may be negative pressure. Where the hollow fibers are microporous, a pressure higher than atmospheric pressure by 770 mmHg, i.e., a pressure of about 10 mmHg, is preferred.

EXPERIMENTAL EXAMPLE

Figure 15:
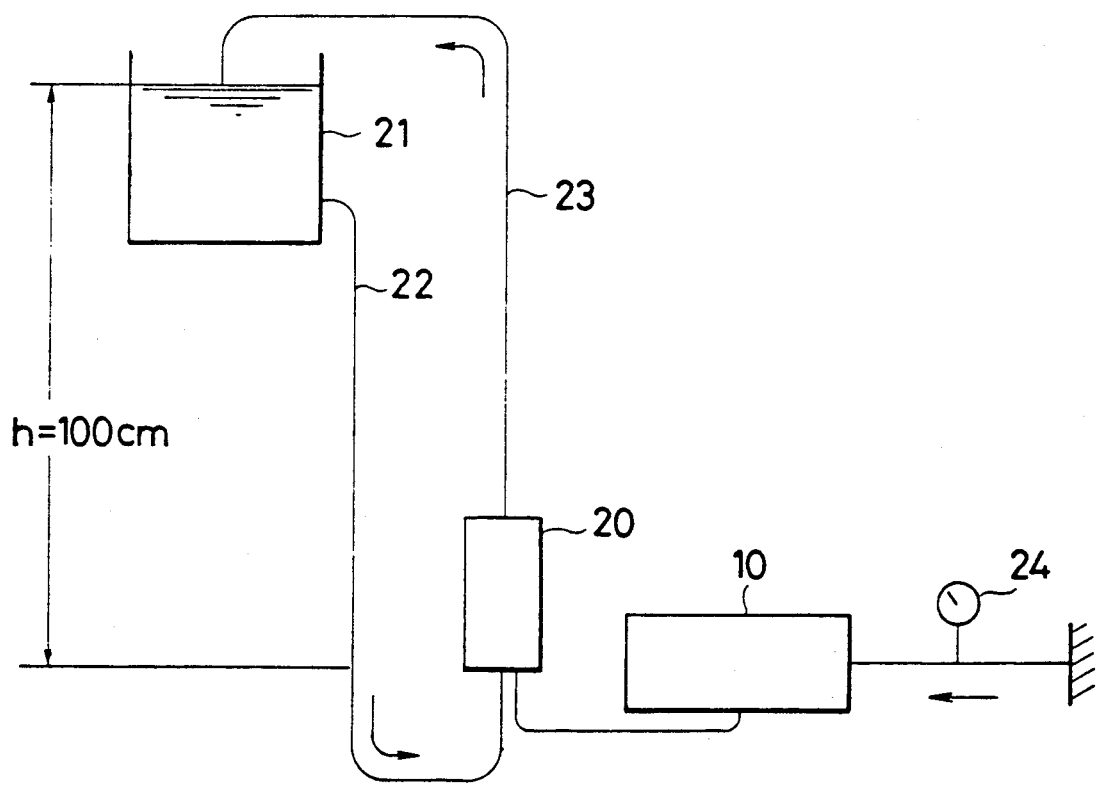
FIG. 15 is a schematic view for explaining operation in the driver circuit of the oxygenator as first embodiment of the invention.

An oxygenator was obtained by basically using a hollow fiber type oxygenator "Capiox II08" (manufactured by Terumo Co., Ltd., with membrane area of 0.8 m$^2$). More specifically, as in the first embodiment, as hollow fibers was used diffusion membrane obtained by filling micropores of porous hollow fiber membrane with silicone resin. As flexible member 6 forming blood in-flow space 4 was used one consisting of silicone rubber and having a thickness of 100 μm. Together with these flexible membranes, operation chambers 8, pressure application controller 10 and check valves 9 and 13 were provided. This oxygenator 20, as shown in FIG. 15, was mounted in a blood circulation circuit including reservoir 21 for supplying blood and conduit tubes 22 and 23 with blood in-flow space 4 down for causing upward blood flow, and it was then primed with 5 U/cc heparin-containing cow blood. The inner diameter of conduit tube 22 was set to 8 mm, the inner diameter of conduit tube 23 was set to 6 mm, and as pressure application controller 10 was used one disclosed in the embodiment. Pressure was reciprocally varied between 0.2 to 0.7 kg/cm$^2$ and atmospheric pressure. The volume of blood inflow space 4 defined by flexible member 6 when open to atmosphere, i.e., the volume of the blood in-flow space of the circuit system when a pressure corresponding to a head of 100 cm was applied to the flexible member, was 32 ml. The fluid pressure pattern application controller 10 was varied with air compressor 24, and the flow rate was measured. As a result, a blood flow rate of 920 ml/min. was obtained with repetition of a cycle of 0.9 sec. of atmospheric pressure and 0.7 sec of a pressure of 0.5 kg/cm as fluid pressure. Neither introduction of bubbles into blood nor rupture of blood cells occurred.

While some preferred embodiments of the invention have been described in the foregoing, these embodiments are by no means limitative, and various changes and modifications are possible without departing from the scope of the invention. For example, while in the first embodiment flexible member 6 was provided on the side of blood in-flow space 4, it is also possible to provide member 6 on the side of blood out-flow space 5 or on each side of blood in- and outflow spaces 4 and 5. In the second embodiment flexible member 6 was provided on each side of blood in- and out-flow spaces 4 and 5, but it is possible to provide the member on either side.

Further, the invention is applicable to apparatus for processing fluid other than blood, for instance industrial water, and also to apparatus for processing gases.

As has been described in the foregoing, the apparatus for processing liquid according to the invention does not require any fluid supply pump. Therefore, unlike the prior art there is no need of assembling the system by connecting apparatus body and pump to each other using tubing or tubes, and therefore, the assembling can be easily obtained. In addition, the area of system installation can be reduced compared to the prior art. Further, there is no problem of leakage or contamination of blood due to cracking of tubes.

Further, fluid is caused to flow through the fluid processor with reciprocation of flexible members, the flow is restricted to be only in one direction by the action of pair port on-off means, and fluid thus can be caused to flow smoothly from fluid inflow space side fluid port to fluid out-flow space side fluid port. Thus, it is possible to prevent stagnation of fluid in the fluid in- and out-flow spaces. Further, there is no need of providing any vein reserver or negative pressure prevention chamber when the apparatus is used as an oxygenator. It is thus possible to eliminate otherwise possible stagnation in the circuit, thus eliminating generation of thrombus and various other undesired phenomena.

Further, in a fluid processing apparatus, which includes port on-off means, fluid pressure supply means and control means for driving this means, further smooth flow of blood from the fluid in-flow space fluid port through the fluid processor to the fluid out-flow space fluid port can be obtained to effectively prevent stagnation or reverse flow of fluid.

Further, enhancement of smooth flow of fluid and prevention of stagnation and reverse flow can be obtained with the method of driving the apparatus for processing fluid according to the invention through repeated execution of sequential steps of on-off operation of the first and second on-off means, switching operation of switching means, communicating/blocking operation of the first and second communicating/blocking means and blocking both the flow paths.

What is claimed is:
1. An apparatus for processing fluid, comprising:
   a housing;
   a fluid processor accommodated in said housing and having a fluid in-flow port and a fluid out-flow port;
   fluid in- and out-flow spaces respectively provided for said respective fluid in- and out-flow ports and having respective fluid ports;
   a pair of wall means defining said respective fluid in- and out-flow spaces;
   a flexible member provided for deformation on at least one of said wall means and capable of being reciprocally deformed to cause processing fluid pressure variations;

an operation chamber provided in correspondence to said flexible member;

fluid pressure supply means for supplying fluid pressure to said operation chamber for causing reciprocal deformation operation of said flexible member; and a pair of port on-off means for communicating and blocking said fluid ports;

said pair of port on-off means including first on-off means for communicating and blocking said fluid in-flow space fluid port and second on-off means for communicating and blocking said fluid out-flow space fluid port; and said fluid pressure supply means including a first pressure source for providing a fluid pressure to said operation chamber, a second pressure source for providing a negative or atmospheric fluid pressure to said operation chamber, a first pressure supply flow path for communicating said first pressure source and said operation chamber with each other, a second pressure supply flow path for communicating said second pressure source and said operation chamber with each other, and switching means for switching said first and second pressure supply flow paths for communicating and blocking.

2. The apparatus for processing fluid according to claim 1, wherein said fluid processor includes a hollow fiber bundle.

3. The apparatus for processing fluid according to claim 1, wherein said port on-off means each comprises of a check valve.

4. The apparatus for processing fluid according to claim 1, which further comprises control means for driving said port on-off means and fluid pressure supply means by sequentially and repeatedly executing:

a first step of rendering said first on-off means to be in a closed state;

a second step executed subsequent or substantially simultaneously to said first step to render said second on-off means to be in an open state and switch said fluid in-flow space side switching means to said first pressure supply flow path;

a third step of rendering said second on-off means to be in a closed state;

a fourth step executed subsequent or substantially simultaneously to said third step to render said first on-off means to be in an open state; and a fifth step executed subsequent or substantially simultaneously to said fourth step to switch said switching means to said second pressure supply flow path.

5. The apparatus for processing fluid according to claim 4, wherein said control means drives said port on-off means; and said fluid pressure supply means further performs other steps of blocking both said flow paths with said switching means after said second step and before said third step and also after said fifth step and before said first step.

6. The apparatus for processing fluid according to claim 1, wherein said switching means includes first switching means on the side of said fluid in-flow space and second switching means on the side of said fluid out-flow space, and which further comprises control means for driving said port on-off means and fluid pressure supply means being driven by sequentially and repeatedly executing:

a first step of rendering said first on-off means to be in a closed state;

a second step of switching said second switching means to said second pressure supply flow path and switching said first switching means to said first pressure supply flow path;

a third step of rendering said second on-off means to be in an open state and switching said second switching means to said first pressure supply flow path;

a fourth step of rendering said second on-off means to be in a closed state;

a fifth step of rendering said first on-off means to be in an open state; and a sixth step of switching said first switching means to said second pressure supply flow path.

7. The apparatus for processing fluid according to claim 6, wherein said control means drives said port on-off means and fluid pressure supply means by further executing a step of blocking both said flow paths with said first switching means and a step of blocking both said flow paths with said second switching means after said second step and before said third step, a step of blocking both said flow paths with said second switching means after said third step and before said fourth step and a step of blocking both said flow paths with said first switching means after said sixth step and before said first step.

8. The apparatus for processing fluid according to claim 1, wherein said switching means includes first switching means on the side of said fluid in-flow space and second switching means on the side of said fluid out-flow space, and which further comprises control means for controlling said port on-off means and fluid pressure supply flow means by sequentially and repeatedly executing:

a first step of rendering said first on-off means to be in a closed state;

a second step of rendering said second on-off means to be in an open state, switching said first switching means to said first pressure supply flow path and switching said second switching means to said first pressure supply flow path;

a third step of rendering said second on-off means to be in a closed state;

a fourth step of rendering said first on-off means to be in an open state;

a fifth step of switching said first switching means to said second pressure supply flow path; and a sixth step of switching said second switching means to said second pressure supply flow path.

9. The apparatus for processing fluid according to claim 8, wherein said control means drives said port on-off means and fluid pressure supply flow path by further executing a step of blocking both said flow paths with said first switching means and a step of blocking both said flow paths with said second switching means after said second step and before said third step and a step of blocking both said flow paths with said first switching means and a step of blocking both said flow paths with said second switching means after said sixth step and before said first step.

10. An apparatus for processing fluid comprising:

a housing;

a fluid processor accommodated in said housing and having a fluid in-flow port and a fluid out-flow port;

fluid in- and out-flow spaces provided for said respective fluid in- and out-flow ports and having respective fluid ports;

a pair of wall means defining said respective fluid in- and out-flow spaces;

a flexible member provided for deformation on said wall means defining said fluid in-flow space and capable of being reciprocally operated to generate pressure variations in processing fluid;

an operation chamber provided in correspondence to said flexible member;

fluid pressure supply flow means for providing a fluid pressure to said operation chamber for causing reciprocal operation of said flexible member; and port on-off means for communicating and blocking said respective fluid ports and directing flow of fluid from said fluid in-flow space to said fluid out-flow space;

said port on-off means including first on-off means for communicating and blocking said fluid in-flow space fluid port and a second on-off means for communicating and blocking said fluid out-flow space fluid port;

said fluid pressure supply means including a first pressure source for providing a positive fluid pressure to said operation chamber, a second pressure source for providing a negative or atmospheric fluid pressure to said operation chamber, a first pressure supply flow path for communicating said first pressure source and said operation chamber with each other, a second pressure supply flow path for communicating said second pressure source and said operation chamber with each other, first communicating/blocking means for communicating and blocking said first pressure supply flow path and second communicating/blocking means for communicating and blocking said second pressure supply flow path;

said apparatus further comprising control means for driving said port on-off means and said fluid pressure supply means by sequentially and repeatedly executing:

a first step of rendering said first on-off means to be in a closed state;

a second step of blocking said second communicating/blocking means after said first step;

a third step of rendering said second on-off means to be in an open state after said second step;

a fourth step of communicating said first communicating/blocking means after said third step;

a fifth step for substantially simultaneously rendering said second on-off means to be in a closed state, blocking said first communicating/blocking means and communicating said second communicating means after said fourth step;

a sixth step of rendering the first on-off means to be in an open state after the fifth step.

11. A method of driving an apparatus for processing fluid;

said apparatus for processing fluid comprising:
a housing;
a fluid processor accommodated in said housing and having a fluid in-flow port and a fluid out-flow port;

fluid in- and out-flow spaces respectively provided for said respective fluid in- and out-flow ports and having respective fluid ports;

a flexible member provided for deformation on at least one of said wall means and capable of being reciprocally deformed to cause fluid pressure variations;

an operation chamber provided in correspondence to said flexible member;

fluid pressure supply means for supplying fluid pressure to said operation chamber for causing reciprocal deformation operation of said flexible member; and a pair of port on-off means for reverse flow prevention, for communicating and blocking said fluid ports and directing the flow of fluid from said fluid in-flow space to said fluid out-flow space;

said port on-off means including first on-off means for communicating and blocking said fluid in-flow space fluid port and second on-off means for communicating and blocking said fluid out-flow space fluid port;

said fluid pressure supply means including a first pressure source for providing a positive fluid pressure to said operation chamber, a second pressure source for providing a negative or atmospheric fluid pressure to said operation chamber, a first pressure supply flow path for communicating said first pressure source and said operation chamber with each other, a second pressure supply flow path for communicating said pressure source and said operation chamber with each other, and switching means for switching said first and second pressure supply flow paths for communicating and blocking;

said port on-off means and fluid pressure supply means being driven by sequentially and repeatedly executing:

a first step of rendering said first on-off means to be in a closed state;

a second step executed subsequent or substantially simultaneously to said first step to render said second on-off means to be in an open state and switch said fluid in-flow space side switching means to said first pressure supply flow means;

a third step of rendering said second on-off means to be in a closed state;

a fourth step executed subsequent or substantially simultaneously to said third step to render said first on-off means to be in an open state; and a fifth step executed subsequent or substantially simultaneously to said fourth step to switch said switching means to said second pressure supply flow path.

12. The method of driving an apparatus for processing fluid according to claim 11, which comprises further steps of blocking both said flow paths with said switching means after said second step and before said third step and also after said fifth step and before said first step.

13. A method of driving an apparatus for processing fluid;

said apparatus for processing fluid comprising:
a housing;
a fluid processor accommodated in said housing and having a fluid in-flow port and a fluid out-flow port;

fluid in- and out-flow spaces respectively provided for said respective fluid in- and out-flow ports and having respective fluid ports a pair of wall means defining said respective fluid in- and out-flow spaces;

a flexible member provided for deformation on at least one of said wall means and capable of being reciprocally deformed to cause fluid pressure variations;

an operation chamber provided in correspondence to said flexible member;

fluid pressure supply means for supplying fluid pressure to said operation chamber for causing reciprocal deformation operation of said flexible member; and a pair of port on-off means for reverse flow prevention, for communicating and blocking said fluid ports and directing the flow of fluid from said fluid in-flow space to said fluid out-flow space;

said port on-off means including first on-off means for communicating and blocking said fluid in-flow space fluid port and second on-off means for communicating and blocking said fluid out-flow space fluid port;

said fluid pressure supply means including a first pressure source for providing a positive fluid pressure to said operation member, a second pressure source for providing a negative or atmospheric fluid pressure to said operation chamber, a first pressure supply flow path for communicating said first pressure source and said operation chamber with each other, a second pressure supply flow path for communicating said second pressure source and said operation chamber with each other, and switching means for switching said first and second pressure supply flow paths for communicating and blocking;

said switching means including first switching means on the side of said fluid in-flow space and second switching means on the side of said fluid out-flow space;

said port on-off means and fluid pressure supply means being driven by sequentially and repeatedly executing:

a first step of rendering said first on-off means to be in a closed state;

a second step of switching said second switching means to said second pressure supply flow path and switching said first switching means to said first pressure supply flow path;

a third step of rendering said second on-off means to be in an open state and switching said second switching means to said first pressure supply flow path;

a fourth step of rendering said second on-off means to be in a closed state;

a fifth step of rendering said first on-off means to be in an open state; and a sixth step of switching said first switching means to said second pressure supply flow path.

14. The method of driving an apparatus for processing fluid according to claim 13, which further comprises a step of blocking both said flow paths with said first switching means and a step of blocking both said flow paths with said second switching means after said second step and before said third step, a step of blocking both said flow paths with said second switching means after said third step and before said fourth step and a step of blocking both said flow paths with said first switching means after said sixth step and before said first step.

15. A method of driving an apparatus for processing fluid:

said apparatus for processing fluid comprising:

a housing;

a fluid processor accommodated in said housing and having a fluid in-flow port and a fluid out-flow port;

fluid in- and out-flow spaces respectively provided for said respective fluid in- and out-flow ports and having respective fluid ports;

a pair of wall means defining said respective fluid in- and out-flow spaces;

a flexible member provided for deformation on at least one of said wall means and capable of being reciprocally deformed to cause fluid pressure variations;

an operation chamber provided in correspondence to said flexible member;

fluid pressure supply means for supplying fluid pressure to said operation chamber for causing reciprocal deformation operation of said flexible member; and a pair of port on-off means for reverse flow prevention, for communicating and blocking said fluid ports and directing the flow of fluid from said fluid in-flow space to said fluid out-flow space;

said port on-off means including first on-off means for communicating and blocking said fluid in-flow space fluid port and second on-off means for communicating and blocking said fluid out-flow space fluid port;

said fluid pressure supply means including a first pressure source for providing a positive fluid pressure to said operation chamber, a second pressure source for providing a negative or atmospheric fluid pressure to said operation chamber, a first pressure supply flow path for communicating said first pressure source and said operation chamber with each other, a second pressure supply flow path for communicating said second pressure source and said operation chamber with each other, and switching means for switching said first and second pressure supply flow paths for communicating and blocking;

said switching means including first switching means on the side of said fluid in-flow space and second switching means on the side of said fluid out-flow space;

said port on-off means and said fluid pressure supply means being driven by sequentially and repeatedly executing:

a first step of rendering said first on-off means to be in a closed state;

a second step of rendering said second on-off means to be in an open state and switching said first switching means to said first pressure supply flow path and switching said second switching means to said first pressure supply flow path;

a third step of rendering said second on-off means to be in a closed state;

a fourth step of rendering said first on-off means to be in an open state;

a fifth step of rendering said first switching means to said second pressure supply flow path; and a sixth step of switching said second switching means to said second pressure supply flow path.

16. The method of driving an apparatus for processing fluid according to claim 15, which further comprises a step of blocking both said flow paths with said first switching means and a step of blocking said flow paths with said second switching means after said second step and before said third step, a step of blocking both said flow paths with said first switching means and a step of blocking both said flow paths with said second switching means after said sixth step and before said first.

17. A method of driving an apparatus for processing fluid,
said apparatus for processing fluid comprising:
a housing;
a fluid processor accommodated in said housing and having a fluid in-flow port and a fluid out-flow port;
fluid in- and out-flow spaces respectively provided for said respective fluid in- and out-flow ports and having respective fluid ports;
a pair of wall means defining said respective fluid in- and out-flow spaces;
a flexible member provided for deformation on said wall means defining said fluid in-flow space and capable of being preciprocally deformed to cause fluid pressure variations;
an operation chamber provided in correspondence to said flexible member;
fluid pressure supply means for supplying fluid pressure to said operation chamber for causing reciprocal deformation operation of said flexible member; and
a pair of port on-off means for reverse flow prevention, for communicating and blocking said fluid ports and directing the flow of fluid from said fluid in-flow space to said fluid out-flow space;
said port on-off means including first on-off means for communicating and blocking said fluid in-flow space fluid port and second on-off means for communicating and blocking said fluid out-flow space fluid port;
said fluid pressure supply means including a first pressure source for providing a positive fluid pressure to said operation chamber, a second pressure source for providing a negative or atmospheric fluid pressure to said operation chamber, a first pressure supply flow path for communicating said first pressure source and said operation chamber with each other, a second pressure supply flow path for communicating said second pressure source and said operation chamber with each other, first communicating/blocking means for communicating and blocking said first pressure supply flow path and second communicating/blocking means for communicating and blocking said second pressure supply flow path;
said port on-off means and said fluid pressure supply means being driven by sequentially and repeatedly executing:
a first step of rendering said first on-off means to be in a closed state;
a second step of blocking said second communicating/blocking means after said first step;
a third step of rendering said second on-off means to be in an open state after said second step;
a fourth step of communicating said first communicating/blocking means after said third step;

a fifth step of substantially simultaneously rendering said second on-off means to be in a closed state, blocking said first communicating/blocking means and communicating said second communicating/blocking means after said fourth step; and
a sixth step of rendering said first on-off means to be in an open state after said fifth step.

18. An apparatus for processing fluid, comprising:
a housing;
a fluid processor accommodated in said housing and having a fluid in-flow port and a fluid out-flow port;
fluid in- and out-flow spaces respectively provided for said respective fluid in- and out-flow ports and having respective fluid ports;
a pair of wall means defining said respective fluid in- and out-flow spaces;
a flexible member provided for deformation on at least one of said wall means and capable of being reciprocally deformed to cause processing fluid pressure variations;
an operation chamber provided in correspondence to said flexible member;
fluid pressure supply means for supplying fluid pressure to said operation chamber for causing reciprocal deformation operation of said flexible member; and
a pair of port on-off means for communicating and blocking said fluid ports;
said pair of port on-off means including first on-off means for communicating and blocking said fluid in-flow space fluid port and second on-off means for communicating and blocking said fluid out-flow space fluid port; and
said fluid pressure supply means including a first pressure source for applying a pressure rise to said operation chamber, a second pressure source for applying a pressure fall to said operation chamber, a first pressure supply flow path for communicating said first pressure source and said operation chamber with each other, a second pressure supply flow path for communicating said second pressure source and said operation chamber with each other, and switching means for switching said first and second pressure supply flow paths for communicating and blocking.

19. The apparatus for processing fluid according to claim 18, which further comprises control means for driving said port on-off means and fluid pressure supply means by sequentially and repeatedly executing:
a first step of rendering said first on-off means to be in a closed state;
a second step executed subsequent or substantially simultaneously to said first step to render said second on-off means to be in an open state and switch said fluid in-flow space side switching means to said first pressure supply flow path;
a third step of rendering said second on-off means to be in a closed state;
a fourth step executed subsequent or substantially simultaneously to said third step to render said first on-off means to be in an open state; and
a fifth step executed subsequent or substantially simultaneously to said fourth step to switch said switching means to said second pressure supply flow path.

20. The apparatus for processing fluid according to claim 19, wherein said control means drives said port on-off means and said fluid pressure supply means further performs other steps of blocking both said flow paths with said switching means after said second step and before said third step and also after said fifth step and before said first step.

21. The apparatus for processing fluid according to claim 18, wherein said switching means includes first switching means on the side of said fluid in-flow space and second switching means on the side of said fluid out-flow space, and which further comprises control means for driving said port on-off means and fluid pressure supply means being driven by sequentially and repeatedly executing:
- a first step of rendering said first on-off means to be in a closed state;
- a second step of switching said second switching means to said second pressure supply flow path and switching said first switching means to said first pressure supply flow path;
- a third step of rendering said second on-off means to be in an open state and switching said second switching means to said first pressure supply flow path;
- a fourth step of rendering said second on-off means to be in a closed state;
- a fifth step of rendering said first on-off means to be in an open state; and
- a sixth step of switching said first switching means to said second pressure supply flow path.

22. The apparatus for processing fluid according to claim 21, wherein said control means drives said port on-off means and fluid pressure supply means by further executing a step of blocking both said flow paths with said first switching means and a step of blocking both said flow paths with said second switching means after said second step and before said third step, a step of blocking both said flow paths with said second switching means after said third step and before said fourth step and a step of blocking both said flow paths with said first switching means after said sixth step and before said first step.

23. The apparatus for processing fluid according to claim 18, wherein said switching means includes first switching means on the side of said fluid in-flow space and second switching means on the side of said fluid out-flow space, and which further comprises control means for controlling said port on-off means and fluid pressure supply flow means by sequentially and repeatedly executing:
- a first step of rendering said first on-off means to be in a closed state;
- a second step of rendering said second on-off means to be in an open state, switching said first switching means to said first pressure supply flow path and switching said second switching means to said first pressure supply flow path;
- a third step of rendering said second on-off means to be in a closed state;
- a fourth step of rendering said first on-off means to be in an open state;
- a fifth step of switching said first switching means to said second pressure supply flow path; and
- a sixth step of switching said second switching means to said second pressure supply flow path.

24. The apparatus for processing fluid according to claim 23, wherein said control means drives said port on-off means and fluid pressure supply flow path by further executing a step of blocking both said flow paths with said first switching means and a step of blocking both said flow paths with said second switching means after said second step and before said third step and a step of blocking both said flow paths with said first switching means and a step of blocking both said flow paths with said second switching means after said sixth step and before said first step.

25. The apparatus for processing fluid according to claim 18, wherein said fluid processor includes a hollow fiber bundle.

26. The apparatus for processing fluid according to claim 18, wherein said port on-off means each comprises of a check valve.

* * * * *